(12) United States Patent  
Francke (10) Patent No.: US 6,556,650 B2
(45) Date of Patent: Apr. 29, 2003

(54) METHOD AND A DEVICE FOR RADIOGRAPHY AND A RADIATION DETECTOR

(75) Inventor: Tom Francke, Sollentuna (SE)

(73) Assignee: XCounter AB, Danderyd (SE)

( * ) Notice: Subject to any disclaimer, the term of this patent is extended or adjusted under 35 U.S.C. 154(b) by 0 days.

(21) Appl. No.: 09/805,018

(22) Filed: Mar. 13, 2001

(65) Prior Publication Data

US 2001/0024484 A1 Sep. 27, 2001

(30) Foreign Application Priority Data

Mar. 22, 2000 (SE) ................................. 0000986

(51) Int. Cl.7 .............................................. G01N 23/04

(52) U.S. Cl. ........................................ 378/62; 378/98.2

(58) Field of Search .......................... 378/62, 98, 98.2, 378/98.8; 250/385.1, 374

(56) References Cited

U.S. PATENT DOCUMENTS

| 4,831,260 A | * | 5/1989 | DiBianca | ................. 250/354.1 |
| 4,937,453 A | * | 6/1990 | Nelson | ................. 250/370.09 |
| 5,308,987 A | | 5/1994 | Wuest et al. | |
| 5,521,956 A | | 5/1996 | Charpak | |
| 5,614,722 A | | 3/1997 | Solberg et al. | |
| 6,337,482 B1 | * | 1/2002 | Francke | ..................... 250/374 |

FOREIGN PATENT DOCUMENTS

SE 513161 C2 5/1999

* cited by examiner

Primary Examiner—David P. Porta
(74) Attorney, Agent, or Firm—Birch, Stewart, Kolasch & Birch, LLP (57) ABSTRACT

A method and apparatus for radiography, and a detector for detecting incident radiation. In the method and the apparatus, wherein X-rays (9) are emitted from an X-ray source (60), the X-rays are formed into a planar beam and are transmitted through an object to be imaged (62), and the X-rays transmitted through said object (62) are detected in a detector chamber(64). The detector chamber (64), which detects incident radiation, including electrode arrangements between which a voltage is applied for creating an electrical field, which may cause electron-ion avalanches of primary and secondary ionisation electrons released by incident radiation. The detector (64) is oriented, in relation to the incident radiation (9), so that the radiation preferably enters sideways between a first and a second essentially parallel plate, between which the electrical field is created. Electrical signals induced by said electron-ion avalanches are detected in at least one detector electrode arrangement, including a plurality of detector electrode elements arranged adjacent to each other, each along a direction being essentially parallel to the incident radiation. Pulses from each detector electrode element are processed in processing electronics, for obtaining values for each pixel corresponding to the respective detector electrode element. The atoms in the detector chamber with which said X-ray photons interacting belong to a liquid, at a temperature between −30° C. and room temperature, or solid material.

59 Claims, 4 Drawing Sheets

METHOD AND A DEVICE FOR RADIOGRAPHY AND A RADIATION DETECTOR

FIELD OF THE INVENTION

The invention relates to a method and apparatus for obtaining radiography images. Moreover it relates to a detector for detecting incident radiation.

BACKGROUND OF THE INVENTION

X-rays have been used in radiographic imaging for a long time, and have been subject to great developments. In its simplest form, imaging is conducted by providing a source of X-ray radiation, an object to be imaged, through which the radiation is transmitted, and a detector for the detection and recording of the transmitted radiation. The X-ray detector used today, at hospitals, is normally a screen-film combination. In a phosphor screen (e.g. $Gd_2O_2S$), X-ray photons are converted and thereby produce secondary light, which is registered on a photographic film. The use of a film limits the dynamic range of the image. The increased efficiency achieved by using a phosphor screen is provided at the expense of the resolution, since the secondary light is emitted isotropically.

To visualise an object within an image, it is necessary that the signal to noise ratio exceeds a certain threshold. The ideal system would have the image noise determined only by photon statistics. This is typically not the case for systems operating with a screen-film combination. To obtain a useful diagnostic image one must increase the patient dose of X-ray radiation.

X-ray photon flux is, by nature, digital. However, one has to distinguish between two different methods in producing digital images:

Integrating technique is an intrinsically analogue method. The response in each pixel is proportional to the total X-ray energy flux. The image is then built up digitally by means of the pixels. Examples of the integrating approach to imaging are CCD (charge-coupled device), storage phosphors, selenium plates, etc. The dynamic range of many of these "digital" detectors is similar to that of film. As in the film technique, the photon flux energy (not the number of photons) is integrated, and thus add noise, since X-ray tubes produce a wide energy spectrum. The most significant noise sources are the "dark current" and the fluctuations in photon energy.

Photon counting is an intrinsically digital method, in which each photon is detected, and detection signals are counted.

A two-dimensional photon counting detector requires many readout elements, and a huge number of interconnections. This leads to typical manufacturing and reliability problems, which has been experienced in such systems. It is difficult to make a large two-dimensional detector with high resolution and high probability for interaction of a major fraction of the X-ray photons.

One way to overcome size and cost limitations, in connection with two-dimensional detector readout systems, is to create an image receptor that is essentially one-dimensional and acquires the second dimension for the image by scanning the X-ray beam and detector across the object to be imaged. Scanning can be done by employing a single line detector and a highly collimated planar X-ray beam. In addition, this approach eliminates the scattered radiation noise but imposes a large heat load on the X-ray tube. To ease the tube loading and simplify the mechanics (by reducing the scanning distance), a multi line set of low cost one-dimensional detectors is beneficial.

One advantage with a line detector is a significant reduction of image noise, which is caused by radiation scattering in the object to be imaged. An X-ray photon that is Compton-scattered in the object will not be detected in a line detector.

Several attempts have been made to develop a photon counting X-ray imaging system based on the scanning technique. This requires detectors that produce fast signals with a rise time of a few nanoseconds. Only a few detection media can produce signals that fast, e.g. a gas or a semiconductor (for example silicon). Semiconductor detectors are expensive and are thus not practical in a multi line configuration. In a gas medium, an X-ray photon interacts with a gas atom which emits a primary ionisation electron, which in [its] turn produces electron-ion pairs that are further multiplied in a gas avalanche. The advantage of a gas detector is low cost, a high noiseless signal amplification in the gas (up to $10^6$), and a uniformity of the detection media.

Several imaging systems described in published articles utilise a multi wire proportional chamber as detector. In its basic configuration, the multi wire proportional chamber consists of a set of thin anode wires stretched between, and parallel with, two cathode planes. Application of a voltage between the anode wires and the cathode planes creates an electric field in the chamber. Electrons emitted in the gas by ionisation of gas atoms, caused by incident X-ray photons, drift towards the anode wires, and when approaching the thin wires they experience ionising interactions, with gas molecules, in the strong electric field. The ensuing avalanche multiplication provides a noiseless amplification of the charge signal, by a factor as large as $10^5$ or more.

An example of a digital imaging system based on photon counting is described in the article, "Multi wire proportional chamber for a digital radiographic installation", by S. E. Baru et. al., in Nuclear Instruments and Methods in Physics Research A, vol. 283 (Nov. 10 1989), pages 431–435. This detector is a combination of a drift chamber and a multi wire proportional chamber with non-parallel anode wires aiming at the focal point of the X-ray source. The radial wires enable the use of a thick interaction volume without parallax error. The uniformity of gain along the anode wires is guaranteed by an increasing gap between the anode wires and the cathode planes.

The described device has, however, the following drawbacks.

The need for providing sufficient space for wire mounting and high voltage isolation results in losses of X-ray detection efficiency.

The use of radial wires to solve the parallax problem results in a position resolution limited by the smallest practical anode wire pitch of about 1 mm. The problem can be overcome by using cathode strip readout that provides the ultimate multi wire proportional chamber resolution. One possibility of a practically feasible fast cathode strip readout is described in the article, "The OD-3 fast one-co-ordinate X-ray detector", by V. M. Aulchenco et. al., in Nuclear Instruments and Methods in Physics Research A, vol. 367 (Dec. 11, 1995), pages 79–82. In this solution, an increasing anode-cathode gap is combined with a decreasing high voltage applied to different anode wire groups.

A known problem with using multi wire proportional chambers for medical imaging is the space charge effect that degrades the detector performance at high X-ray fluxes above 10 kHz/mm². To decrease the space charge effect, the anode plane has been modified by adding alternating cathode wires in a prior art device, disclosed in U.S. Pat. No. 5,521,956 (G. Charpak).

The use of thin wires (typically less than 100 µm in diameter) in multiwire proportional chambers makes them difficult to construct, and reduces reliability, since one broken wire disables operation of the whole detector.

A gas avalanche detector that is very simple in construction and does not use anode wires is the gaseous parallel plate avalanche chamber. This detector is basically a gas-filled capacitor, comprising two essentially parallel conducting plates, an anode and a cathode, subjected to a high voltage. The high voltage is chosen such that electrons released by ionisation in the gas produce avalanches in a strong electric field between the plates. Typically, the distance between the plates is on the order of one millimetre, and the field strength is in the order of kilovolts per millimetre, depending on the type of gas used. A wide variety of gases can be used depending on the application. In such a detector X-ray photons are incident on a plane parallel to the detector plane, or on the cathode, which is made of a material that emits electrons, so called photoelectrons, when X-ray photons interact with it.

An important advantage over the multi wire proportional chamber, is that the electrostatic field in a gaseous parallel plate avalanche chamber is not concentrated around single thin wires, but is essentially constant over the entire amplification volume. This results in a very short drift time of positive ions across the amplification gap, thus drastically reducing the space charge effect.

An example of using a gaseous parallel plate avalanche chamber for radiographic imaging is described in the article, "A parallel plate chamber with pixel readout for very high data rate", by F. Angelini et. al., in IEEE Transactions on Nuclear Science, vol. 36 (February 1989) pages 213–217. In the two-dimensional readout configuration described, it is difficult to achieve high X-ray conversion efficiency despite the addition of a drift chamber in front of a parallel plate chamber to increase the thickness of the gas layer.

Another device, disclosed in U.S. Pat. No. 5,308,987 (Wuest et. al.), utilises a cathode made of a high atomic number material to improve the conversion efficiency in a parallel plate chamber used in a two-dimensional readout configuration. The low yield of photoelectrons from the high atomic number material results in a reduction of X-ray ray detection efficiency.

Another important difference from a multi wire proportional chamber is that the gas amplification factor strongly depends on the distance from the primary ionisation charge to the anode, resulting in a poor energy resolution and signal detection efficiency, in prior used gaseous parallel plate avalanche chambers. Due to this problem, prior devices were unable to use the gas amplification gap in gaseous parallel plate avalanche chambers as an X-ray conversion volume.

In SE 9704015-8 [has] this limitation been overcome by providing a well collimated planar beam incident essentially sideways on the detector.

A general drawback with gaseous X-ray detectors relates to the fact that the X-ray flux coming from the X-ray source is divergent. In a thick conversion volume this divergence causes a parallax error. Most methods proposed to minimise the parallax error are difficult to implement in practice.

SUMMARY OF THE INVENTION

It is an object of the present invention to provide a detector for use in radiography, which overcomes or at least reduces the above mentioned problem.

According to the present invention this object is obtained by providing a method for obtaining improved images in radiography comprising:

emitting X-rays from an X-ray source, transmitting said X-rays through an object to be imaged, detecting the X-rays transmitted through said object in a chamber, the depth of which, in the direction of the incident radiation, is such as to permit interaction of a major fraction of the incident X-ray photons with atoms of a liquid material, at a temperature between −30° C. and room temperature, or solid material in said chamber, for the production of primary ionisation electron-ion pairs, within a detector including electrode arrangements between which a voltage is applied for creating an electrical field, detecting electrical signals in at least one detector electrode arrangement, said electrical signals being induced by said electron-ion pairs, in at least one of a plurality of detector electrode elements arranged adjacent to each other, and An apparatus for use in radiography, comprising an X-ray source, a chamber, the depth of which, in the direction of the incident radiation, is such as to permit interaction of a major fraction of the incident X-ray photons with atoms of a liquid material, at a temperature between −30° C. and room temperature, or solid material in said chamber, for the production of primary ionisation electron-ion pairs, within a detector including electrode arrangements between which a voltage is applied for creating an electrical field for detecting the X-ray photons transmitted through said object, and a plurality of detector electrode elements being arranged adjacent to each other and also by a detector for detecting incident radiation, including electrode arrangements between which a voltage is applied for creating an electrical field, a chamber, the depth of which, in the direction of the incident radiation, is such as to permit interaction of a major fraction of the incident X-ray photons with atoms in said chamber, for the production of primary ionisation electron-ion pairs, within a detector including electrode arrangements between which a voltage is applied for creating an electrical field for detecting the X-ray photons transmitted through said object.

An advantage of the present invention is that the detector exhibits fast response with pulse widths less than 10 nanoseconds and as fast as 1 nanosecond.

Another advantage of the present invention is that the detector can be made thinner compared to a similar gaseous detector.

Yet another advantage of the present invention is that the detector is less sensitive to the direction of the incident X-rays compared to similar gaseous detectors with respect to the resolution of the image from the radiated object detected by the detector.

Further objects and advantages are attained by further features in the appended claims.

DESCRIPTION OF PREFERRED EMBODIMENTS

Figure 1:
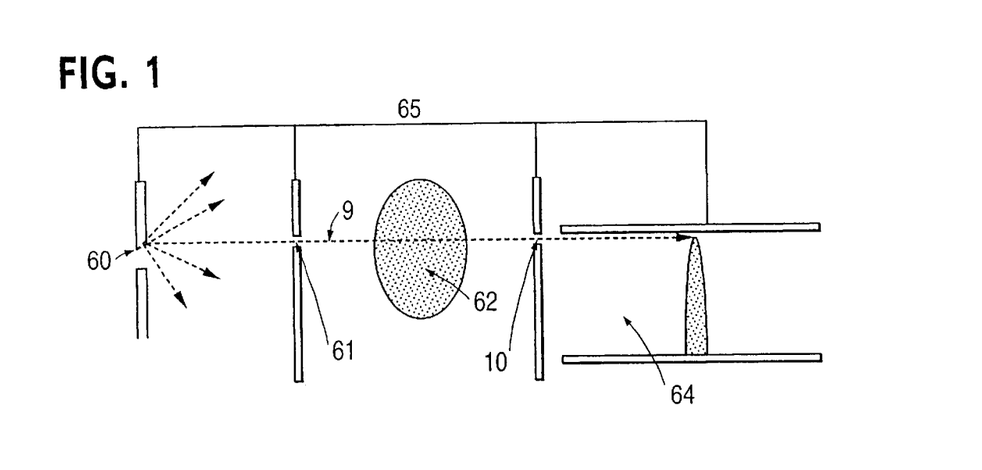
FIG. 1 illustrates schematically, in an overall view, an apparatus for planar beam radiography, according to the invention.

FIG. 1 is a sectional view in a plane orthogonal to the plane of a planar X-ray beam 9 of an apparatus for planar beam radiography, according to the invention. The apparatus includes an X-ray source 60, which together with a first thin collimator window 61 produce the planar fan-shaped X-ray beam 9, for irradiation of an object 62 to be imaged. The first thin collimator window 61 can be replaced by other means for forming an essentially planar X-ray beam, such as an X-ray diffraction mirror or an X-ray lens etc. The beam transmitted through the object 62 enters a detector 64, optionally through a thin slit or second collimator window 10, which is aligned with the X-ray beam. A major fraction of the incident X-ray photons are detected in the detector 64, which includes a detector chamber, orient ed, in this embodiment, so that the X-ray photons enter sideways between, and essentially parallel with two essentially parallel plates. The X-ray photons may alternatively enter the detector chamber from any direction of a half sphere 17 which is symmetric around a normal vector of the cathode plan as shown for example in FIG. 2.

The detector and its operation will be further described below. The X-ray source 60, the first thin collimator window 61, the optional collimator window 10 and the detector chamber 64 are connected and fixed in relation to each other by, for example, a frame or support 65. The so formed apparatus for radiography can be moved as a unit to scan an object which is to be examined. In a single detector system, as shown in FIG. 1, the scanning is preferably done by a pivoting movement, rotating the unit around an axis through for example the X-ray source 60 or the detector 64. The location of the axis depends on the application or use of the apparatus, and possibly the axis can also run through the object 62, in some applications.

An apparatus and a method according to this invention is especially advantageous in imaging a part of a body of a patient, e.g. in mammography.

The detector chamber, is generally composed of two essentially parallel plates constituting two limiting walls of the chamber. Said plates are subjected to a strong electric field, which is generated by applying a high voltage. A volume defined as a region or gap between said plates is filled with a liquid material, at a temperature between −30° C. and room temperature, or a solid material.

An X-ray photon incident into the liquid material, at a temperature between −30° C. and room temperature, or solid material produces an electron-ion pair upon interaction with an atom in said volume. This production may be caused by photo effect, Compton-effect or Auger-effect. The primary electron so produced loses its kinetic energy through interactions with new atoms, causing the production of further new electron-ion pairs, typically a few hundreds, whereof the electrons are called secondary ionisation electrons.

The secondary ionisation electrons may then be amplified by electron-ion avalanches depending on the strength of the electric field. When the electric field between the plates is low, no (or very little) electron-ion avalanche amplification takes place. Above a well defined electric field strength electron-ion avalanche amplification can start and can reach amplifications up to 100 or more. The electric field is preferably in the region to cause avalanche amplification, but the present invention will also work for said lower electrical field range, i.e. not high enough to cause electron-ion avalanches.

The movements of the electrons and ions induce electrical signals in the electrodes. Those signals are typically picked up in one or both of the electrodes and are further amplified and processed by a readout circuitry to obtain an accurate measurement of the X-ray photon interaction point and, optionally the X-ray photon energy.

In a preferred embodiment of the invention, the X-rays to be detected are incident sideways on the detector in a direction essentially parallel to the parallel plates, and may enter the detector through a thin slit or collimator window in case of liquid material, at a temperature between −30° C. and room temperature, between said plates. Said thin slit or collimator window may be omitted in the case of solid material between said plates. In this way the anode and/or the cathode plates does not have to be pervious to the X-ray photons. In an alternative embodiment of the invention, the X-rays to be detected are incident anywhere from a half sphere with respect to one of the plates on the detector. This alternative embodiment may require that the cathode plates are, at least to some degree, pervious to the X-ray photons, since the X-rays may go through said cathode in order to interact with the material in the detector chamber.

Figure 2:
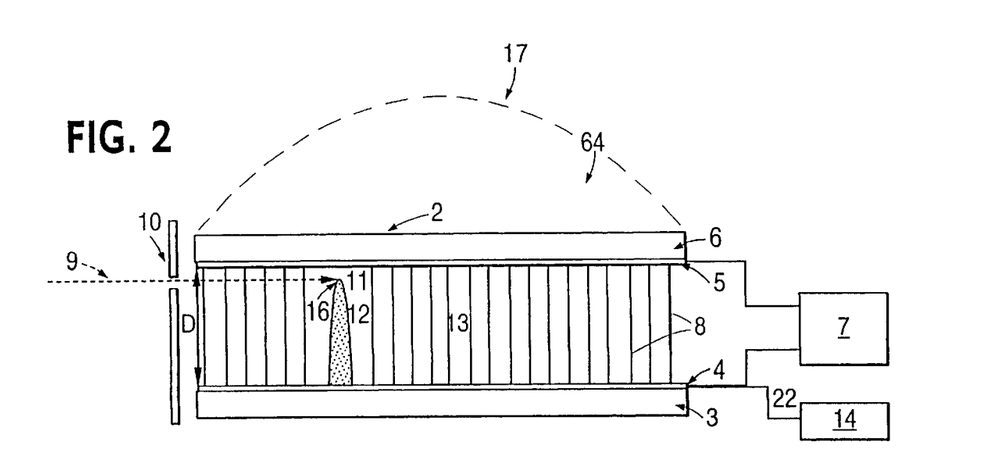
FIG. 2 is a schematic cross sectional view of a first embodiment of a detector chamber according to the invention.

Referring to FIG. 2, a first embodiment of a detector according to the invention, is shown, and designated the reference number 64. This detector chamber includes an anode plate 1 and a cathode plate 2, being mutually essentially parallel and separated by a thin gap or region 13 defining as mentioned above a volume. Said volume is filled with a liquid material at a temperature between −30° C. and room temperature or a solid material, being for example TMP (Trimethylpentane) TME (Trimethylethane), cadmium zinc telluride (CdZnTe), or silicon, germanium or other types of semiconductors.

The anode plate 1 includes a substrate 3, made of for example glass or ceramics, having a thickness of preferably 0.1–10 mm, and an anode electrode 4 arranged thereon in the form of a coating of a conductive material, for example metal, having a thickness of preferably 0.01–10 µm.

For better adhesion to the substrate 3 and for better layer stability, the electrode 4 may include several metal layers, each with a different thickness and material, for example vanadium, copper and nickel. When the substrate 3 is made of glass, the first layer is preferably of chromium, which has good adhesion properties to glass as well as to the subsequent metal layers. The electrode 4 may also include a layer of resistive material, for example silicon monoxide, deposited on top of the metal layer(s).

Likewise, the cathode plate 2 includes a substrate 6 with a coating 5, similar to what is described about the anode 1. Both the anode electrode 4 and the cathode electrode 5 can be segmented into strips parallel and/or orthogonal to the incoming X-ray beam.

The important characteristics of the liquid material, at a temperature between −3020 C. and room temperature, or solid material is on the first hand that said materials are capable of being ionised when influenced by X-ray photons and on the other hand that said materials exhibit a relatively low electron affinity. Low electron affinity makes it possible for an electron to travel a long distance without being absorbed.

The anode electrode 4 and the cathode electrode 5 are connected to a high voltage DC power supply 7, for producing a uniform electric field 8, in the gap or region 13 between the essentially parallel plates 1 and 2. As an example, the gap or region 13 has a height D (distance between the parallel plates 1 and 2) of 10–1000 μm, and the voltage V applied between the electrodes 4 and 5 is 1000–100, [.]000 V. The voltage applied creates an electric field E between the electrodes 4 and 5, that is equal E=V/D.

In operation, X-rays 9 are incident on the detector 64 from any direction of a half sphere with respect to a cathode 2 or an anode 1 in said electrode arrangements. In FIG. 2 the X-ray photons are incident on the detector by essentially sideways. The incident X-rays 9 enter the detector 64 through an optional thin slit or collimator window 10 close to the cathode plate 2, and travel through the volume in a direction essentially parallel to the cathode plate 2. X-ray photons produce a primary ionisation electron-ion pair within the volume as a result of interaction with an atom of the liquid material, at a temperature between −30° C. and room temperature, or solid material therein. Each primary electron 11 produced loses its kinetic energy through interactions with atoms causing further production of electron-ion pairs (secondary ionisation electron-ion pairs). Typically a few thousand secondary ionisation electron-ion pairs are produced from a 20 keV X-ray photon in this process. The secondary ionisation electrons 16 (together with the primary ionisation electron 11) are accelerated in the high electric field, in a direction towards the anode plate 1. The accelerated electrons 11, 16 interact with other atoms in the gap 13 causing further electron-ion pairs to be produced. Those produced electrons will also be accelerated in the field, and will interact with new atoms, causing further electron-ion pairs to be produced. This process continues during the travel of the electrons towards the anode 1 and an avalanche 12 will be formed.

For primary ionisation electrons emitted at a distance H from the anode 1, the overall charge gain is given by M=exp(αH), where α is the first Townsend coefficient pertinent to the liquid material, at a temperature between −3020 C. and room temperature, or solid material and field conditions. Under proper choices of material, e.g. one of those mentioned above, and electrical field, gains from 2–100 and more can be achieved. Under the influence of the strong electric field, the electrons in the avalanche volume will move towards the anode, while the ions will move towards the cathode 2. Due to the fact that the strong electric field is uniform over the gap and the height D of the gap 13 is very small, a very short drift time of the positive ions across the amplification volume is achieved, which drastically reduces space charge effects.

The movement of charges in the gap 13 induces electrical charges on the anode electrode 4 as well as on the cathode electrode 5. The induced charges can be detected, for example, by means of the anode electrode 4 coupled to a charge sensitive pre-amplifier, which converts the charge pulses into a current or voltage pulse that can be further processed in processing electronics 14, also including said pre-amplifier.

Possibly, the cathode electrodes or a separate detector electrode arrangement can be used for the detection in a similar way.

It is to be noted that each incident X-ray photon that interacts with an atom will cause an avalanche 12, which is to be detected if the applied electrical field is high enough. In order to achieve a high detection efficiency where a major fraction of the X-ray photons causes avalanches, the length of the detector chamber, in the direction of the incident X-ray photons, must be chosen to give a high probability for interaction between the X-ray photons and atoms of the material in the volume 13. The probability of interaction increases with increasing length of the gaseous parallel plate avalanche chamber. The definition of length is either the orthogonal distance between the plates, the length of the detector as measured parallel with said plates or a distance being neither orthogonal or parallel with said plates.

Figure 3:
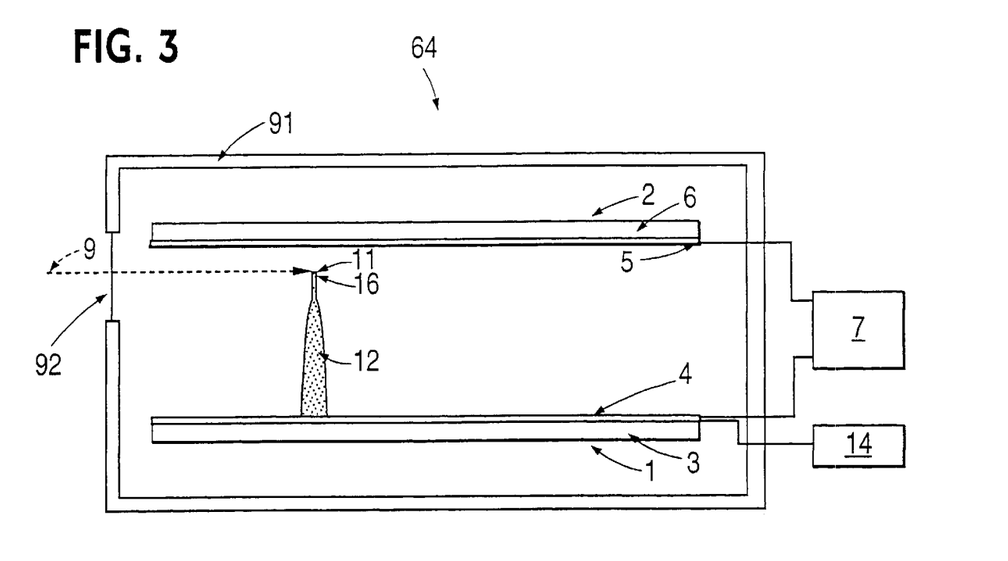
FIG. 3 is a schematic cross sectional view of a detector chamber, according to the invention, contained in a housing.

As mentioned, the detector chamber 64 contains a solid material or liquid material, at a temperature between −30° C. and room temperature. Therefore, in case of liquid material at a temperature between −3020 C. and room temperature, the detector includes a leak-proof housing 91 with a slit entrance window 92, through which the X-ray beam 9 enters the detector, as illustrated in FIG. 3. The window is made of a material which is essentially transparent to the radiation, e.g. Mylar®, or a thin aluminium foil. This is a particularly advantageous additional effect of the invention, detecting essentially sideways incident beams in the detector chamber 64, compared to detector chambers, which are designed for radiation incident substantially perpendicular to the parallel plates or in any direction of a half sphere with respect to the cathode 2 or anode 1, requiring a window covering a large area or a cathode material pervious to said X-rays. The window 92 can in this way be made thinner, thus reducing the number of X-ray photons absorbed in the window 92 or absorbed by the cathode material.

Figure 4:
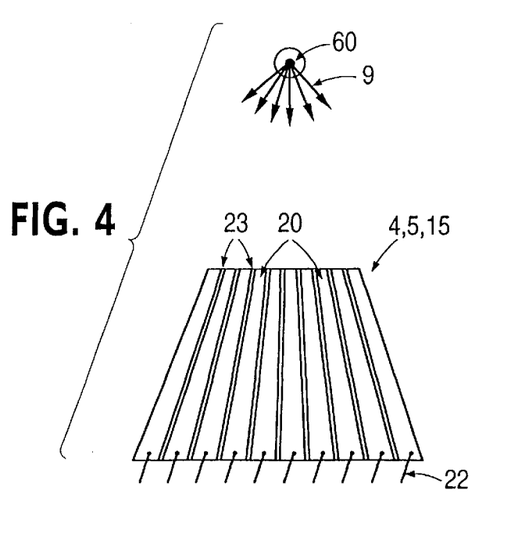
FIG. 4 is a schematic top view of a first embodiment of an X-ray source and an electrode formed by readout strips.

The electrode arrangement shown in FIG. 4 is preferably the anode 1, but alternatively or conjointly the cathode 2 can have the described construction. In the alternative embodiment of FIG. 3 the detector electrode arrangement 15 may be formed as shown in FIG. 4. In that case, the anode electrode 4 is formed as an unitary electrode without strips and spacings. The same is valid for the cathode electrode or the anode electrode, respectively, when only the other thereof comprises the detector electrode arrangement.

Figure 5:
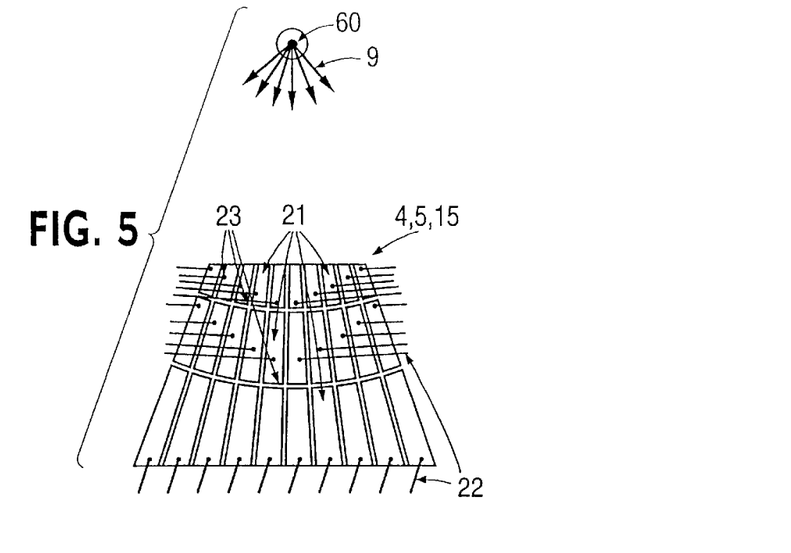
FIG. 5 is a schematic top view of a second embodiment of an X-ray source and an electrode formed by segmented readout strips.

In FIG. 5, an alternative configuration of an electrode is shown. The strips have been divided into segments 21, electrically insulated from each other. Preferably a small spacing extending perpendicular to the incident X-rays is provided between each segment 21 of respective strip. Each segment is connected to the processing electronics 14 by means of signal conductors 22, where the signals from each segment preferably are processed separately. As in FIG. 4, where the anode or cathode electrode constitute the detector electrode, the signal conductors 22 also connect the respective strip(s) to the high voltage DC power supply 7.

This electrode can be used when the energy of each X-ray photon is to be measured, since an X-ray photon having higher energy statistically causes a primary ionisation after a longer path through the material than an X-ray photon of lower energy. By means of this electrode, both the position of X-ray photon interaction and the energy of each X-ray photon can be detected.

Generally in all embodiments, each incident X-ray photon causes one induced pulse in the detector electrode. The pulses are processed in the processing electronics, which eventually shapes the pulses, and integrate or count the pulses from each strip representing one pixel. The pulses can also be processed so as to provide an energy measure for each pixel.

Where the detector electrode is on the cathode side the area of an induced signal is broader (in a direction perpendicular to the direction of incidence of the X-ray photons) than on the anode side. Therefore, weighing of the signals in the processing electronics is preferable.

The fact that the amplitude of an induced signal to be measured, which is a result of an interaction between an X-ray photon and an atom of the material in the volume 13, strongly depends on the distance from the starting point of the avalanche to the anode electrode, places demands on the alignment of the collimator windows 61, 10 and the anode electrode 4. The desired condition is a planar beam parallel with the anode electrode. These tight demands can be eased by a detector with a configuration shown in FIG. 6.

Figure 6:
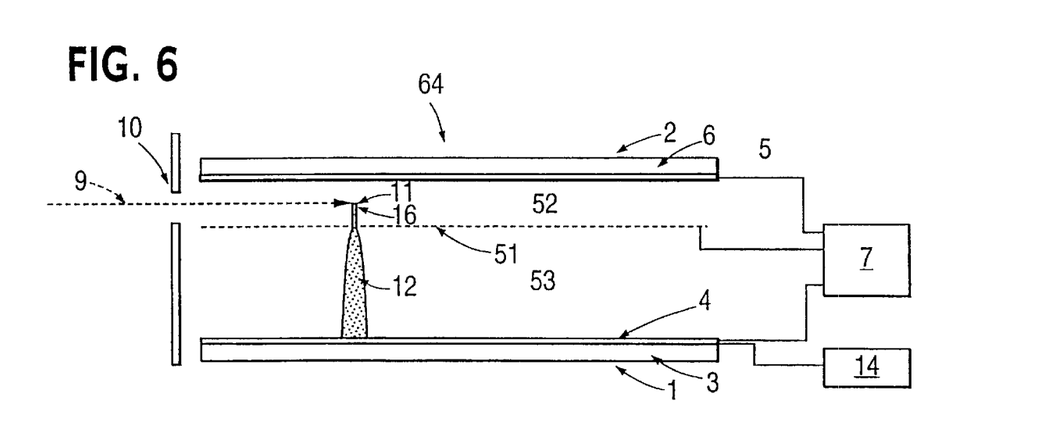
FIG. 6 is a schematic cross sectional view of a second embodiment of a detector chamber according to the invention.

An electrically conductive mesh or grid 51 arranged between and essentially parallel with the anode and the cathode plates, divides the gap into a drift chamber 52 for X-ray conversion and a parallel plate avalanche chamber 53 for amplification. Both chambers may be filled with the same liquid material, at a temperature between −30° C. and room temperature, and the separating mesh serves as a cathode for the parallel plate avalanche chamber 53, and as an anode for the drift chamber 52. If solid material is in the volume 13 the mesh is either integrated in said semiconducting material or in between two separated parts of said solid material preferably in a low pressure environment.

A weak electric field is created between the cathode electrode 5 and the mesh 51 by means of the power supply 7. In this weak field, the secondary ionisation electrons produced by the primary ionisation electrons (together with the same) can drift towards the mesh 51. A high voltage is further applied between the mesh 51 and the anode electrode 4, which results in a strong electric field. This field may attract the electrons to pass through the mesh 51, and passing the mesh 51 they may start an electron-ion avalanche 12, as described above. The other parts of the detector are also the same as described above. It is important that the distance between the mesh 51 and the anode electrode is essentially uniform, since the amplification is strongly dependent on the distance from the starting point of the avalanche, here the mesh 51, to the anode electrode. The alignment of the X-ray beam 9 and the parallelity of the cathode electrode is not critical.

Figure 7:
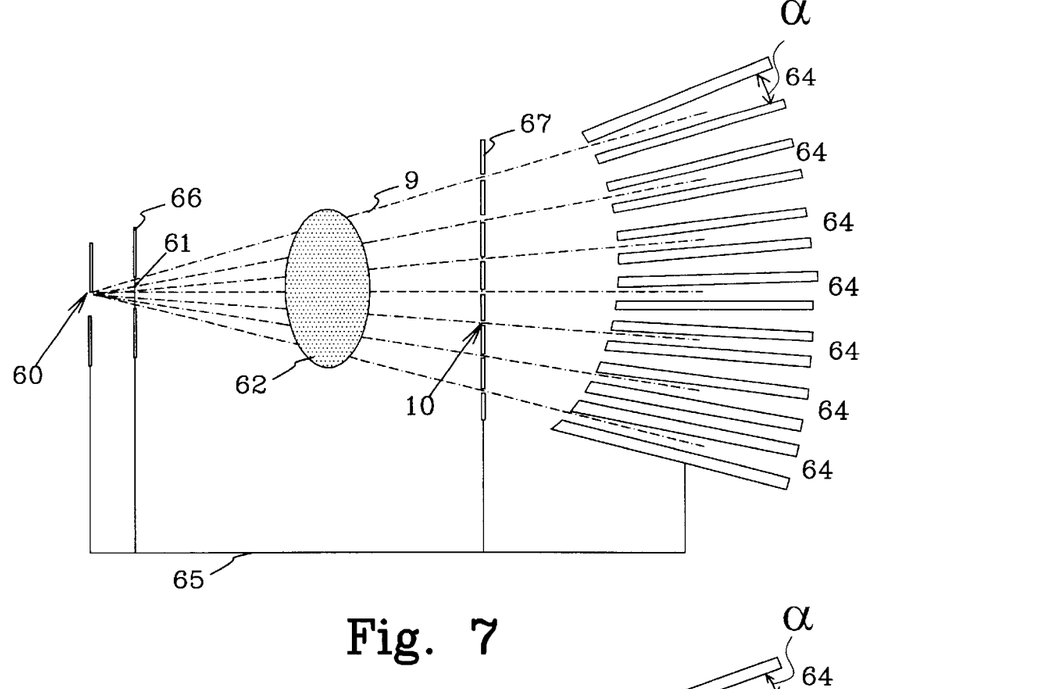
FIG. 7 is a schematic cross sectional view of an embodiment according to the invention, with stacked detectors

FIG. 7 shows schematically an embodiment of the invention with a plurality of the inventive detectors 64 stacked, one on top of another. By this embodiment a multiline scan can be achieved, which reduces the overall scanning distance, as well as the scanning time. The apparatus of this embodiment includes an X-ray source 60, which together with a number of collimator windows 61 produce a number of planar fan-shaped X-ray beams 9, for irradiation of the object 62 to be imaged. The beams transmitted through the object 62 optionally enter the individual stacked detectors 64 through a number of second collimator windows 10, which are aligned with the X-ray beams. The first collimator windows 61 are arranged in a first rigid structure 66, and the optional second collimator windows 10 are arranged in a second rigid structure 67 attached to the detectors 64, or arranged separately on the detectors.

By choosing the angle α between the anode plate 1 and the cathode plate 2 of each detector, the detectors can be stacked with the surfaces of the detectors facing each other being parallel, when the detectors are aligned with the X-ray source. This facilitates the manufacturing of the multiline detector, since no special steps for aligning and adjustment is needed. The stability of the detector is also increased, while the number of parts is reduced. Preferably the stacked detectors are accommodated in one common housing 91. It can be advantageous if the cathodes 2 of the two adjacent detectors face each other, and that the anodes 1 of two adjacent detectors face each other. In such a case the cathodes and/or anodes of two adjacent detectors can be formed into common elements for two adjacent detectors. If they are accommodated in separate housings also the outer walls of each housing exhibit an angle α (i.e. one wall is parallel with the anode plate 1 and one wall is parallel with the cathode plate 2).

Said angle α is in the range of $0<\alpha\leq 90$, preferably $1/160°–6°$

The X-ray source 60, the rigid structure 66, and the possible structure 67 including collimator windows 61, 10, respectively, and the stacked detectors 64, which are fixed to each other, are connected and fixed in relation to each other by for example a frame or support 65. The so formed apparatus for radiography can be moved as a unit to scan an object, which is to be examined. In this multiline configuration, the scanning can be done in a transverse movement, perpendicular to the X-ray beam, as mentioned above. It can also be advantageous if the apparatus for radiography is fixed and the object to be imaged is moved.

A further advantage of using a stacked configuration, compared to large single volume gas detectors, is reduction of background noise caused by X-ray photons scattered in the object 62. These scattered X-ray photons travelling in directions not parallel to the incident X-ray beam could cause "false" signals or avalanches in one of the other detectors 64 in the stack, if passing through anode and cathode plates and entering such a chamber. This rejection is achieved by significant absorption of (scattered) X-ray photons in the material of the anode and the cathode plates, or the collimator 67.

Figure 8:
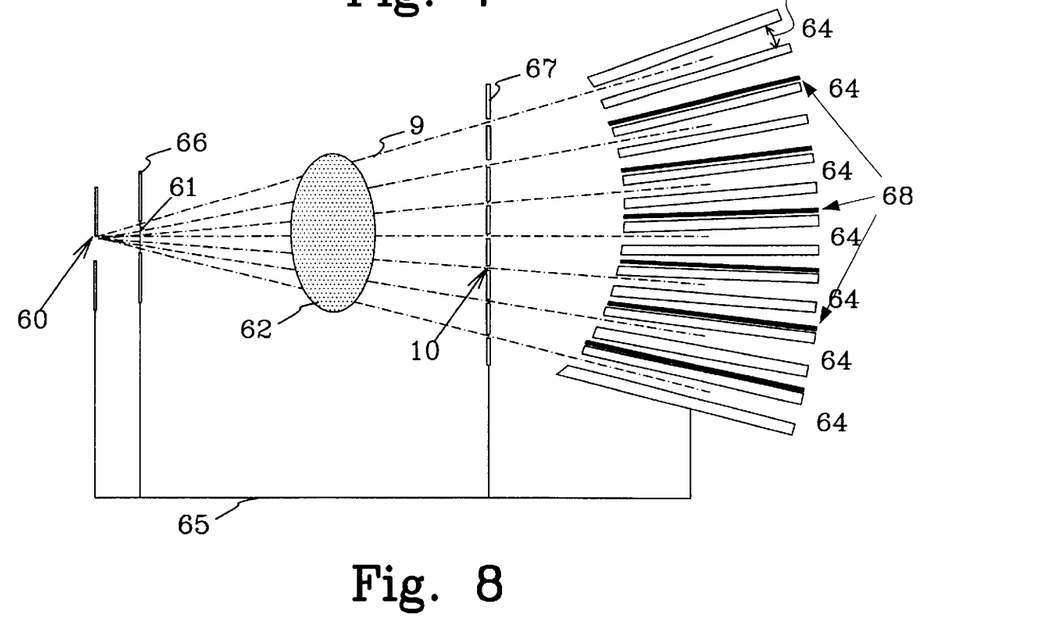
FIG. 8 is a schematic cross sectional view of a further embodiment according to the invention, with stacked detectors.

This background noise can be further reduced by providing thin absorber plates 68 between the stacked detectors 64, as shown in FIG. 8. The stacked detector is similar to that of FIG. 7, with the difference that thin sheets of absorbing material is placed between each adjacent detectors 64. These absorber plates or sheets can be made of a high atomic number material, for example tungsten.

Although the invention has been described in conjunction with a number of preferred embodiments, it is to be understood that various modifications may still be made without departing from the spirit and scope of the invention, as defined by the appended claims.

What is claimed is:

1. A method for obtaining a radiography image, said method comprising the steps of:
    emitting X-rays from an X-ray source into a chamber in any direction of a half sphere, which is symmetric around a normal vector of a cathode plan, with respect of a cathode or an anode in electrode arrangements;
    transmitting said X-rays through an object to be imaged;
    detecting the X-rays transmitted through said object in said chamber, the depth of which, in the direction of the incident radiation, is such as to permit interaction of a major fraction of the incident X-ray photons with atoms of a liquid, at a temperature between −30° C. and room temperature, or solid material in said chamber, for the production of primary ionization electron-ion pairs, within a detector including said electrode arrangements between which a voltage is applied for creating an electrical field;

applying the voltage to said electrode arrangements in said detector for creating an electrical field which causes electron-ion avalanches of primary and secondary ionization electrons released by said incident X-ray photons; and detecting electrical signals in at least one detector electrode arrangement, said electrical signals being induced by said electron-ion pairs, in at least one of a plurality of detector electrode elements arranged adjacent to each other.

2. The method of claim 1, wherein the liquid or the solid material is selected from the group consisting of TMP (Trimethylpentane) TME (Trimethylethane), cadmium zinc telluride (CdZnTe), silicon, germanium or a semiconductor.

3. The method according to claim 1, wherein pulses from each detector electrode element are processed in processing electronics for obtaining energy values for each pixel corresponding to the respective detector electrode element.

4. The method according to claim 1, further comprising the steps of:

arranging a mesh between and essentially parallel to a first and a second plate; and applying a voltage, substantially lower than the voltage between the electrode arrangements, between the first electrode arrangement and the mesh, in order to create a conversion and drift volume and an amplification volume.

5. The method according to claim 4, wherein the detector electrode elements are elongated, formed by strips arranged side by side and electrically insulated from each other and included in at least one of said first and second plates.

6. The method according to claim 1, wherein pulses from each detector electrode element are counted separately in processing electronics for obtaining values for each pixel corresponding to the respective detector electrode element.

7. The method according to claim 1, wherein pulses from each detector electrode element are integrated separately in processing electronics for obtaining values for each pixel corresponding to the respective detector electrode element.

8. An apparatus for use in radiography, comprising:

an X-ray source, wherein emitted X-rays from the X-ray source enter a chamber from any direction of a half sphere, which is symmetric around a normal vector of a cathode plan, with respect to a cathode or anode in electrode arrangements;

a chamber, the depth of which, in the direction of the incident radiation, is such as to permit interaction of a major fraction of the incident X-ray photons with atoms of a liquid, at a temperature between −30° C. and room temperature, or solid material in said chamber, for the production of primary ionization electron-ion pairs, within a detector including said electrode arrangements between which a voltage is applied for creating an electrical field for detecting the X-ray photons transmitted through said object; and a plurality of detector electrode elements being arranged adjacent to each other.

9. The apparatus of claim 8, wherein the liquid or the solid material is selected from the group consisting of TMP (Trimethylpentane) TME (Trimethylethane), cadmium zinc telluride (CdZnTe), silicon, germanium or a semiconductor.

10. The apparatus for use in planar beam radiography according to claim 9, wherein each detector electrode element is connected to processing electronics, wherein pulses from each detector electrode element are processed in processing electronics for obtaining energy values for each pixel corresponding to the respective detector electrode element.

11. The apparatus for use in radiography according to claim 8, wherein the voltage applied between said electrode arrangements in said detector is high enough for creating an electrical field which causes electron-ion avalanches of primary and secondary ionization electrons released by said incident X-ray source.

12. The apparatus for use in radiography according to claim 8, further comprising:

a first parallel plate, said first parallel plate including a first substrate carrying a first electrode arrangement; and a second parallel plate, said second parallel plate including a second substrate carrying a second electrode arrangement, wherein the first and second electrode arrangements are carried on surfaces of the first and second substrate, respectively, facing each other.

13. The apparatus for use in radiography according to claim 12, wherein the first electrode arrangement is a cathode;

the second electrode arrangement is an anode; and the detector electrode elements are elongated, formed by strips arranged side by side and electrically insulated from each other are carried by the second substrate, on the surface opposite to the anode electrode.

14. The apparatus for use in radiography according to claim 12, wherein the first electrode arrangement is a cathode;

the second electrode arrangement is an anode, formed of said detector electrode elements are elongated, formed by strips arranged side by side and electrically insulated from each other; and each longitudinal edge of the strips is essentially parallel to the incident radiation.

15. The apparatus for use in radiography according to claim 12, wherein the first electrode arrangement is a cathode, formed of said detector electrode elements which are elongated, formed by strips arranged side by side and electrically insulated from each other;

the second electrode arrangement is an anode; and each longitudinal edge of the strips is essentially parallel to the incident radiation.

16. The apparatus for use in radiography according to claim 13, wherein two of the edges of each strip are aimed at the X-ray source.

17. The apparatus for use in radiography according to claim 13, wherein the strips are divided, perpendicular to the incident X rays, into sections electrically insulated from each other.

18. The apparatus for use in radiography according to claim 12, wherein a mesh is arranged between and parallel to the first and the second plate; and a voltage, substantially lower than the voltage between the electrode arrangements, is applied between the first electrode arrangement and the mesh, in order to create a conversion and drift volume and an amplification volume.

19. The apparatus for use in radiography according to claim 8, wherein the X-ray source and the chamber are fixed in relation to each other in order to form a unit, which can be used for scanning an object.

20. The apparatus for use in radiography according to claim 8, wherein
   a number of chambers are stacked to form a detector unit;
   a device for forming an essentially planar X-ray beam is arranged for each chamber, said device being positioned between said X-ray source and the object to be imaged; and
   the X-ray source, said device for forming a essentially planar X-ray beam and said detector unit are fixed in relation to each other in order to form a unit, which can be used for scanning an object.

21. The apparatus for use in planar beam radiography according to claim 20, wherein absorber plates are arranged between the plates in the chambers in order to absorb scattered X-ray photons.

22. The apparatus for use in planar beam radiography according to claim 8, wherein each detector electrode element is connected to processing electronics, wherein pulses from each detector electrode element are counted separately for obtaining values for each pixel corresponding to the respective detector electrode element.

23. The apparatus for use in planar beam radiography according to claim 8, wherein each detector electrode element is connected to processing electronics, wherein pulses from each detector electrode element are integrated separately in processing electronics for obtaining values for each pixel corresponding to the respective detector electrode element.

24. A detector for detecting incident radiation, comprising:
   electrode arrangements between which a voltage is applied for creating an electrical field;
   a chamber, the depth of which, in the direction of the incident radiation, is such as to permit interaction of a major fraction of the incident X-ray photons with atoms of a liquid, at a temperature between −30° C. and room temperature, or solid material in said chamber, said emitted X-rays from the X-ray source entering the chamber from any direction of a half sphere, which is symmetric around a normal vector of a cathode plan, with respect to a cathode or anode in said electrode arrangements, for the production of primary ionization electron-ion pairs, within a detector including electrode arrangements between which a voltage is applied for creating an electrical field for detecting the X-ray photons transmitted through said object, said voltage applied between said electrode arrangements in said detector being high enough for creating an electrical field which causes electron-ion avalanches of primary and secondary ionization electrons released by said incident X-ray source; and
   a plurality of detector electrode elements arranged adjacent to each other.

25. The detector of claim 24, wherein the liquid or the solid material is selected from the group consisting of TMP (Trimethylpentane) TME (Trimethylethane), cadmium zinc telluride (CdZnTe), silicon, germanium or a semiconductor.

26. The detector according to claim 24, wherein each detector electrode element is connected to processing electronics, wherein pulses from each detector electrode element are integrated separately in processing electronics for obtaining values for each pixel corresponding to the respective detector electrode element.

27. The detector according to claim 24, wherein each detector electrode element is connected to processing electronics, wherein pulses from each detector electrode element are processed in processing electronics for obtaining energy values for each pixel corresponding to the respective detector electrode element.

28. The detector according to claim 24, further comprising:
   a first parallel plate, said first parallel plate including a first substrate carrying a first electrode arrangement; and
   a second parallel plate, said second parallel plate including a second substrate carrying a second electrode arrangement,
   wherein the first and second electrode arrangements are carried on surfaces of the first and second substrate, respectively, facing each other.

29. The detector according to claim 28, wherein
   the first electrode arrangement is a cathode;
   the second electrode arrangement is an anode; and
   the detector electrode elements are elongated, formed by strips arranged side by side and electrically insulated from each other are carried by the second substrate, on the surface opposite to the anode electrode.

30. The detector according to claim 28, wherein
   the first electrode arrangement is a cathode;
   the second electrode arrangement is an anode, formed of said detector electrode elements which are elongated, formed by strips arranged side by side and electrically insulated from each other; and
   each longitudinal edge of the strips is essentially parallel to the incident radiation.

31. The detector according to claim 28, wherein
   the first electrode arrangement is a cathode, formed of said detector electrode elements which are being elongated, formed by strips arranged side by side and electrically insulated from each other
   the second electrode arrangement is an anode; and
   each longitudinal edge of the strips is essentially parallel to the incident radiation.

32. The detector according to claim 29, wherein two of the edges of each strip are aimed at the source of radiation.

33. The detector according to claim 29, wherein the strips are divided, perpendicular to the incident radiation, into sections electrically insulated from each other.

34. The detector according to claim 24, wherein
   a mesh is arranged between and parallel to a first and a second plate; and
   a voltage, substantially lower than the voltage between the electrode arrangements, is applied between the first electrode arrangement and the mesh, in order to create a conversion and drift volume and an amplification volume.

35. The detector according to claim 24, wherein each detector electrode element is connected to processing electronics, wherein pulses from each detector electrode element are counted separately for obtaining values for each pixel corresponding to the respective detector electrode element.

36. An apparatus for use in planar beam radiography, comprising:
   a radiation source, for emitting an incident radiation source; and
   a gaseous avalanche detector, including a chamber into which the incident radiation is emitted so that the radiation enters the chamber and a majority of the incident radiation interacts with atoms of a liquid, at a temperature between −30° C. and room temperature, or solid material in the chamber for the production of primary ionization electron-ion pairs, within the gaseous avalanche detector and a mesh, arranged between and substantially parallel to a first and a second plate, wherein a voltage, substantially lower than the voltage between at least two electrode arrangements, is applied between a first of the at least two electrode arrangements and the mesh, in order to create a conversion and drift volume and an amplification volume.

37. An apparatus for use in planar beam radiography, comprising:

a radiation source, for emitting an incident radiation source; and a gaseous avalanche detector, including a chamber into which the incident radiation is emitted so that the radiation enters the chamber and a majority of the incident radiation interacts with atoms of a liquid, at a temperature between −30° C. and room temperature, or solid material in the chamber for the production of primary ionization electron-ion pairs, within the gaseous avalanche detector.

38. An apparatus for use in planar beam radiography, comprising:

a radiation source, for emitting an incident radiation source; and a gaseous avalanche detector, including a chamber into which the incident radiation is emitted so that the radiation enters the chamber substantially sideways between a first and a second essentially parallel plate, and in which a voltage is applied for creating an electrical field, wherein the electrical field causes electron-ion avalanches of primary and secondary ionization electrons released by the incident radiation, wherein a majority of the incident radiation interacts with atoms of a liquid, at a temperature between −3020 C. and room temperature, or solid material in the chamber for the production of primary ionization electron-ion pairs, within the gaseous avalanche detector.

39. The apparatus of claim 38, wherein the liquid or the solid material is selected from the group consisting of TMP (Trimethylpentane) TME (Trimethylethane), cadmium zinc telluride (CdZnTe), silicon, germanium or a semiconductor.

40. The apparatus of claim 36, wherein the liquid or the solid material is selected from the group consisting of TMP (Trimethylpentane) TME (Trimethylethane), cadmium zinc telluride (CdZnTe), silicon, germanium or a semiconductor.

41. The apparatus for use in radiography according to claim 38, wherein the emitted X-rays from the X-ray source enters the chamber from any direction of a half sphere, which is symmetric around a normal vector of a cathode plan, with respect to a cathode or anode in said electrode arrangements.

42. The apparatus for use in radiography according to claim 38, wherein the voltage applied between said electrode arrangements in said detector is high enough for creating an electrical field which causes electron-ion avalanches of primary and secondary ionization electrons released by said incident X-ray source.

43. The apparatus for use in radiography according to claim 38, wherein said first parallel plate includes a first substrate carrying a first electrode arrangement;

said second parallel plate includes a second substrate carrying a second electrode arrangement; and the first and second electrode arrangements are carried on surfaces of the first and second substrate, respectively, facing each other.

44. The apparatus for use in radiography according to claim 38, wherein the first electrode arrangement is a cathode;

the second electrode arrangement is an anode; and the detector electrode elements are elongated, formed by strips arranged side by side and electrically insulated from each other are carried by the second substrate, on the surface opposite to the anode electrode.

45. The apparatus for use in radiography according to claim 38, wherein the first electrode arrangement is a cathode;

the second electrode arrangement is an anode, formed of said detector electrode elements are elongated, formed by strips arranged side by side and electrically insulated from each other; and each longitudinal edge of the strips is essentially parallel to the incident radiation.

46. The apparatus for use in radiography according to claim 38, wherein the first electrode arrangement is a cathode, formed of said detector electrode elements which are elongated, formed by strips arranged side by side and electrically insulated from each other;

the second electrode arrangement is an anode; and each longitudinal edge of the strips is essentially parallel to the incident radiation.

47. The apparatus for use in radiography according to claim 36, wherein the emitted X-rays from the X-ray source enters the chamber from any direction of a half sphere, which is symmetric around a normal vector of a cathode plan, with respect to a cathode or anode in said electrode arrangements.

48. The apparatus for use in radiography according to claim 36, wherein the voltage applied between said electrode arrangements in said detector is high enough for creating an electrical field which causes electron-ion avalanches of primary and secondary ionization electrons released by said incident X-ray source.

49. The apparatus for use in radiography according to claim 36, wherein said first plate includes a first substrate carrying a first electrode arrangement;

said second plate includes a second substrate a carrying the second electrode arrangement; and the first and second electrode arrangements are carried on surfaces of the first and second substrate, respectively, facing each other.

50. The apparatus for use in radiography according to claim 36, wherein the first electrode arrangement is a cathode;

the second electrode arrangement is an anode; and the detector electrode elements are elongated, formed by strips arranged side by side and electrically insulated from each other are carried by the second substrate, on the surface opposite to the anode electrode.

51. The apparatus for use in radiography according to claim 36, wherein the first electrode arrangement is a cathode;

the second electrode arrangement is an anode, formed of said detector electrode elements are elongated, formed by strips arranged side by side and electrically insulated from each other; and each longitudinal edge of the strips is essentially parallel to the incident radiation.

52. The apparatus for use in radiography according to claim 36, wherein the first electrode arrangement is a cathode, formed of said detector electrode elements which are elongated, formed by strips arranged side by side and electrically insulated from each other;

the second electrode arrangement is an anode; and each longitudinal edge of the strips is essentially parallel to the incident radiation.

53. The apparatus for use in radiography according to claim 37, wherein the emitted X-rays from the X-ray source enters the chamber from any direction of a half sphere, which is symmetric around a normal vector of a cathode plan, with respect to a cathode or anode in said electrode arrangements.

54. The apparatus for use in radiography according to claim 37, wherein the voltage applied between said electrode arrangements in said detector is high enough for creating an electrical field which causes electron-ion avalanches of primary and secondary ionization electrons released by said incident X-ray source.

55. The apparatus for use in radiography according to claim 37, further comprising:

a first parallel plate, said first parallel plate including a first substrate carrying a first electrode arrangement; and a second parallel plate, said second parallel plate including a second substrate a carrying the second electrode arrangement, wherein the first and second electrode arrangements are carried on surfaces of the first and second substrate, respectively, facing each other.

56. The apparatus for use in radiography according to claim 37, wherein the first electrode arrangement is a cathode;

the second electrode arrangement is an anode; and the detector electrode elements are elongated, formed by strips arranged side by side and electrically insulated from each other are carried by the second substrate, on the surface opposite to the anode electrode.

57. The apparatus for use in radiography according to claim 37, wherein the first electrode arrangement is a cathode;

the second electrode arrangement is an anode, formed of said detector electrode elements are elongated, formed by strips arranged side by side and electrically insulated from each other; and each longitudinal edge of the strips is essentially parallel to the incident radiation.

58. The apparatus for use in radiography according to claim 37, wherein the first electrode arrangement is a cathode, formed of said detector electrode elements which are elongated, formed by strips arranged side by side and electrically insulated from each other;

the second electrode arrangement is an anode; and each longitudinal edge of the strips is essentially parallel to the incident radiation.

59. The apparatus of claim 37, wherein the liquid or the solid material is selected from the group consisting of TMP (Trimethylpentane) TME (Trimethylethane), cadmium zinc telluride (CdZnTe), silicon, germanium or a semiconductor.

* * * * *